(12) United States Patent
Stauffer et al.

(10) Patent No.: US 6,605,137 B2
(45) Date of Patent: Aug. 12, 2003

(54) AMMONIA COMPOSITION AND PROCESS THEREFOR AND THEREWITH

(75) Inventors: Timothy P. Stauffer, Beaumont, TX (US); Gregory P. Shankwitz, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/855,344

(22) Filed: May 15, 2001

(65) Prior Publication Data

US 2002/0001558 A1 Jan. 3, 2002

Related U.S. Application Data

(60) Provisional application No. 60/205,756, filed on May 19, 2000.

(51) Int. Cl.[7] .............................................. B01D 19/04
(52) U.S. Cl. ......................................... 95/155; 558/319
(58) Field of Search ............................ 558/319; 95/155

(56) References Cited

U.S. PATENT DOCUMENTS

| 2,905,597 A |   | 9/1959 | Stafford et al. |
|---|---|---|---|
| 3,666,681 A | * | 5/1972 | Keil et al. .................. 252/358 |
| 3,936,360 A |   | 2/1976 | Wu |
| 4,584,125 A | * | 4/1986 | Griswold et al. ........... 252/358 |

FOREIGN PATENT DOCUMENTS

JP           052326979        *  9/1993

* cited by examiner

*Primary Examiner*—Ceila Chang
*Assistant Examiner*—Kamal Saeed

(57) ABSTRACT

A composition, a process for producing the composition, and a process for producing a nitrile are disclosed. The composition is substantially anhydrous or free of water and comprises ammonia and an anti-foaming agent. The composition can be produced by contacting substantially anhydrous ammonia with an anti-foaming amount of an anti-foaming agent. The process for producing a nitrile comprises contacting a hydrocarbon with the composition disclosed herein.

20 Claims, No Drawings

AMMONIA COMPOSITION AND PROCESS THEREFOR AND THEREWITH

FIELD OF THE INVENTION

The present invention relates to a composition comprising ammonia and an anti-foaming agent, to a process for substantially suppressing foaming during the vaporization of ammonia, and to a process for using the vaporized ammonia for producing chemicals.

BACKGROUND OF THE INVENTION

Ammonia can be used in a variety of industrial applications. Typical chemical compounds that can be produced from ammonia include hydrogen cyanide, amines, nitriles and nitric acid.

Hydrogen cyanide can be produced from natural gas, ammonia, and oxygen over a platinum/rhodium gauze catalyst at a temperature greater than 1000° C. (the "Andrussow Process"). Hydrogen cyanide can also be produced from methane and ammonia passed through porous ceramic tubes lined or coated with platinum, at about 1300° C. (the "BMA" process). Still further hydrogen cyanide can be produced from propane and ammonia in the presence of an electric current, typically at temperatures greater than 1500° C. (the "Shawinigan Process").

Nitriles and derivatives can be produced from ammonia and a hydrocarbon, for example, in the catalytic ammoxidation of propylene to form acrylonitrile. Nitriles are important industrial chemicals, especially in the plastics, surface coatings, and adhesive industries. For example, acrylonitrile and methacrylonitrile can be used to produce acrylic fiber, as an intermediate in the syntheses of antioxidants, pharmaceuticals, dyes and surface active agents.

Ammonia is generally supplied to the processes by either direct pipeline or barge transfer. Ammonia supplied to and taken from storage tanks has a high foaming potential, which may be due to a threshold concentration of one or more impurities contained therein—these impurities can be present either from concentration in the ammonia process or due to impurities received from barge transfers.

Before entering the reactors for producing hydrogen cyanide or a nitrile, for example, the ammonia feed may be flashed or heated to convert it from liquid state to vapor state. The ammonia feed can also be mixed with other feeds and heated. Heating or flashing ammonia to produce ammonia vapor, particularly at low pressures such as, for example, below 100 psig (about 700 kPa), results in foaming situations. This foam can result in various process limitations, such as, for example, low vaporizer capacity, carryover of material to downstream equipment, such as reactors, resulting in catalyst damage and high manufacturing costs, unstable flow control, inappropriate material on the inlet side of relief valves, which is a safety hazard.

It is well known in the ammonia industry that ammonia contains small quantities of oil, mostly occurring from compressor seal leakage. Water is also present in many cases to prevent corrosion. Suggested causes of foam include the oil, detergents present in the oil, water, non-condensable gases such as $CO_2$, $N_2$, $H_2$, and non-volatile materials such as iron. Eliminating the oil via dry seals on compressors on barges and in the ammonia production unit may be considered, but is an expensive option and, since the actual cause for foaming is unknown, dry seals may not offer a real solution.

Therefore, there is an ever-increasing need to develop a process for handling ammonia to produce an ammonia that is substantially free of, or has reduced, foam potential.

SUMMARY OF THE INVENTION

According to the first embodiment of the invention a composition is provided, comprising ammonia and an anti-foaming agent wherein the composition is substantially free of water or is substantially anhydrous. This composition is especially effective when using ammonia that has concentrated levels of impurities from an ammonia synthesis process or ammonia that has been retrieved from ammonia storage tanks.

According to a second embodiment of the invention, a process that can be used for vaporizing ammonia is provided. The process comprises contacting an ammonia-containing fluid with a foam-suppressing amount of an anti-foaming agent wherein the fluid is substantially free of water or is substantially anhydrous and subsequently vaporizing the ammonia by known means.

According to a third embodiment of the invention, a process for use of ammonia vapor in a chemical process is provided. The process comprises contacting, in the presence of an ammoxidation catalyst, an oxygen-containing fluid, a hydrocarbon and an ammonia vapor composition.

DETAILED DESCRIPTION OF THE INVENTION

The term "fluid" used herein refers to liquid, gas, or combination thereof. The term "gas" includes vapor. The term "substantially" denotes "more than trivial". The term "anti-foaming agent" refers to a chemical that, when added to a fluid, can substantially reduce the surface activity of the fluid thereby substantially preventing the fluid from foaming. The terms "anti-foaming agent" and "anti-foam" can be used interchangeably. The term "substantially free of water" means less than about 5, preferably less than about 3, and most preferably less than about 1 weight % water, based on the total weight of the composition to which the term refers.

This invention applies to any process where liquid ammonia is being vaporized or heated prior to utilization of the ammonia.

According to the first embodiment of the invention, a fluid composition comprising, consisting essentially of, or consisting of ammonia and an anti-foaming agent is provided.

The ammonia can be any ammonia, i. e., liquid ammonia, gaseous ammonia, or combinations thereof. The ammonia is advantageously ammonia that has concentrated levels of impurities from an ammonia synthesis process, referred to herein as "cold ammonia" or ammonia that has been retrieved from ammonia storage tanks, "storage ammonia". Cold ammonia is defined herein to mean ammonia from an ammonia synthesis process wherein the pressure has been let down to near atmospheric in order to provide process cooling and to allow for storage. Storage ammonia is defined herein to mean ammonia comprising cold ammonia from ammonia synthesis as well as added ammonia from barges, tank cars, etc., which is stored in storage tanks at atmospheric pressure and temperature below −30° C., at a location accessible to subsequent chemical processing. Warm ammonia herein means ammonia from an ammonia synthesis process wherein the ammonia stream is taken off some intermediate location of the final flash stages such that the resulting pressure of the liquid stream is substantially higher than atmospheric pressure and is generally at ambient temperature conditions. Cold ammonia typically contains impurities from the ammonia process. Storage tank ammonia typically will contain the same impurities as cold ammonia in addition to water, oils, etc. due to contamination from transfers. Cold ammonia and storage ammonia have been found to develop severe foaming problems when vaporized for introducing into subsequent chemical processes.

Any anti-foaming agent that can substantially prevent an ammonia-containing fluid from foaming, especially during vaporization of the fluid, used in the invention. Generally such anti-foaming agents include, but are not limited to, silicones, siloxanes, especially polydimethylsiloxane, hydrocarbon oils such as decane, and combinations thereof. The presently preferred anti-foaming agent is polydimethylsiloxane for it is readily available and effective. For uses wherein the vaporized ammonia is subsequently used in the presence of a platinum-based catalyst, it is preferred that the anti-foaming agent is free of hydrocarbon oils.

Generally, the anti-foaming agent can be present in the composition in a foam-suppressing amount, which is the amount that can substantially reduce the surface activity of ammonia. Such foam-suppressing amount can be in the range of from about 1 to 5000, preferably about 5 to 4000, and most preferably 5 to 3000 mg/kg (ppm) of ammonia. Generally, the concentration of the anti-foaming agent can depend on the ammonia quality and the amount of blow-down taken from the vaporizer. Blowdown is defined herein to mean the amount of material drawn from the bottom of a vaporizer during vaporization.

The composition can be produced by any methods known to one skilled in the art such as, for example, mixing the anti-foaming agent with ammonia. According to the second embodiment of the invention, the process for producing the composition of ammonia and an anti-foaming agent comprises, consists essentially of, or consists of contacting an ammonia-containing fluid with a foam-suppressing amount of an anti-foaming agent wherein the fluid is substantially free of water. Typically the ammonia will have a temperature in the range of about −33° C. to about 15° C. Cold ammonia and storage ammonia will typically be pre-heated to a temperature of 8–15° C. before contacting with the anti-foam. Contemporaneously with, or after, contacting the ammonia with the anti-foam, the resulting mixture is treated under conditions effective to vaporize the ammonia.

Conditions effective to vaporize the ammonia/anti-foam mixture should be sufficient to effect the suppression of foaming during vaporization. Generally, conditions can include heating to a temperature in the range of from about 0 to 30, preferably 0 to about 20 and most preferably 0 to 10° C., under a pressure that accommodates the temperature range, and for a period of time in the range from 1 second to about 10 hours.

Upon completion of the vaporizing, the anti-foaming agent can be separated and recovered, by any means known to one skilled in the art, for reuse. The fluid containing ammonia and the anti-foaming agent can also be used as such in a process such as that disclosed hereinbelow. By vaporizing the ammonia/anti-foam composition, such that foaming does not occur advantages are gained in subsequent chemical processes, such as stable flow control during times when cold ammonia or storage tank ammonia is being fed to the process, reduction/elimination of downstream catalyst damage, increasing holding capacity of vessels and improving efficiency of evaporation equipment, thereby increasing productivity in a chemical process, without needing to add costs.

According to the third embodiment of the invention, a process is provided herein for producing a product wherein the process comprises use of ammonia vapor that has been treated with an anti-foam prior to vaporization. In one example, a process comprises, consists essentially of, or consist of contacting, in the presence of an ammoxidation catalyst, an oxygen-containing fluid, a hydrocarbon and an ammonia vapor composition to produce a nitrile. Said ammonia vapor composition is prepared by vaporizing a composition comprising ammonia and an anti-foaming agent as described above.

According to the invention, the term "nitrile" refers to a compound having the formula of RCN in which R is hydrogen or an organic radical having 1 to about 10 carbon atoms per radical. The presently preferred nitrites are acrylonitrile, hydrogen cyanide, methacrylonitrile, and derivatives thereof, or combinations thereof. The hydrocarbon can be methane, ethylene, propylene, propane, isobutylene, butene, pentene, 2-methyl-butene, 2-methyl-pentene, hexene, or combinations of two or more thereof.

The contacting of a hydrocarbon with ammonia and an oxygen-containing fluid is generally carried out in the gas phase in a suitable vessel such as, for example, a fluidized bed reactor having an air compressor and a quench column. A hydrocarbon such as, for example, propylene and the ammonia/anti-foam composition can be vaporized and introduced into the vessel or reactor.

The molar ratio of hydrocarbon to ammonia can be any ratio so long as a nitrile can be produced. Generally, the molar ratio can be in the range of from about 0.1:1 to about 10:1, preferably about 0.2:1 to about 5:1, and most preferably about 0.5:1 to about 2:1. The contacting can be carried out under any suitable condition such as a temperature in the range of from about 250 to about 600, preferably about 300 to about 550, and most preferably about 350 to about 500° C., under a pressure that can accommodate the temperature range, and for a time sufficient to produce a nitrile, generally about 0.01 second to about 2 hours.

Ammoxidation catalysts are well-known in the art and typically multi-component mixed metal oxides, especially based on bismuth-molybdenum oxides. The preferred catalyst is a typical Bi/Mo-based catalyst supported on an inorganic support such as, for example, silica. The contacting produces a product mixture comprising a nitrile, if R does not equal H, and hydrogen cyanide, generally in gas or vapor phase.

The product mixture can be further purified by any means known to one skilled in the art such as that disclosed in U.S. Pat. No. 3,936,360. Because the purification is well known, the description of which is omitted herein.

Any oxygen-containing fluid that comprises about 1 to about 100 weight % oxygen can be used. Air is a preferred fluid. The most preferred is compressed air.

In a second example, a process comprises, consists essentially of, or consist of contacting, in the presence of platinum-based catalyst, an oxygen-containing fluid, and an ammonia vapor composition to produce nitric acid. The ammonia vapor composition is prepared by vaporizing a composition comprising ammonia and an anti-foaming agent as described above.

In a third example, a process comprises, consists essentially of, or consist of contacting, a hydrocarbon, and an ammonia vapor composition at a temperature greater than 1000° C. to produce hydrogen cyanide. The ammonia vapor composition is prepared by vaporizing a composition comprising ammonia and an anti-foaming agent as described above. In a first embodiment, the hydrocarbon is preferably natural gas and the process is performed in the presence of a platinum/rhodium gauze catalyst and oxygen. In a second embodiment, the hydrocarbon is methane and the process in performed in the presence of platinum coated porous ceramic tubes. In a third embodiment, the hydrocarbon is propane and the process is performed in the presence of an electric current.

The following examples are intended to illustrate the invention and are not to be construed to unduly limit scope of the invention.

EXAMPLE 1

The compositions of various ammonia sources were determined. The results are shown in Table 1. Samples 1 to 7 employed storage ammonia, runs 8–9 employed cold ammonia which is ammonia coming from an ammonia process and feeding the atmospheric storage tank, and runs 10–11 employed warm ammonia which is also ammonia coming from an ammonia process which goes into pipeline supply. Samples were then tested for their potential for foaming.

TABLE 1[a]

| Run Number | Ammonia % | Chloride ppm | $CO_2$ ppm | NVR % | Oil ppm | Water % | Iron ppm |
|---|---|---|---|---|---|---|---|
| 1 | 99.74 | 0.2 | 8 | 0.01 | 4.3 | 0.26 | 0.3 |
| 2 | 99.83 | 0.2 | 24 | 0.01 | 6.9 | 0.17 | 0.1 |
| 3 | 99.81 | 0.2 | 4 | 0.01 | 4.43 | 0.19 | 0.1 |
| 4 | 99.67 | 0.2 | 97 | 0.01 | 4.95 | 0.33 | 0.1 |
| 5 | 99.97 | 0.2 | 72 | 0.01 | 2.6 | 0.03 | 0.1 |
| 6 | 99.96 | 0.2 | 4 | 0.01 | 3.39 | 0.32 | 0.1 |
| 7 | 99.99 | 0.2 | 85 | 0.06 | 4.3 | 0.01 | 0.1 |
| 8 | 99.8 | 0.2 | 28 | 0.01 | 3.26 | 0.2 | |
| 9 | 99.9 | 0.2 | 15 | 0.01 | 2.86 | 0.1 | |
| 10 | 99.6 | 0.2 | 16 | 0.01 | 4.69 | 0.4 | |
| 11 | 99.8 | 0.2 | 23 | 0.01 | 3.12 | 0.2 | |

[a]The values shown are either weight % or parts per million by weight; and NVR denotes non-volatile residue.

Runs to determine foaming were carried out in an ammonia bomb connected by tubing to two stainless steel sight glasses rated for 2315 psi (about 16205 kpa) at 100° C. (37.8° C.). One sight glass was used as a blank while the other was for the actual test. Ammonia was inventoried into the sight glasses from a sample bomb at ambient conditions. Anti-foam was added through a septum between the bomb and the sight glasses. A vacuum hose was used to pull initial vacuum on the system prior to inventorying with ammonia and to allow for proper venting of the ammonia during the experiment.

Each sight glass was filled with about 20 ml of ammonia. Anti-foaming agent were added to the test sight glass to various concentrations shown in Table 2. Isopropyl alcohol was used to reduce the viscosity, if needed, of the anti-foaming agent so that a syringe sample could be taken. Qualitative definitions used in Table 2 are: (1) none—no foaming present; (2) very small initial amount—initially when the ammonia is flashed off, about one-fourth of the sight glass height is filled with foam; (3) small amount—foaming occurs to slightly less than one half the sight glass height; and (4) moderate amount—foaming occurs to approximately one-half the sight glass height.

TABLE 2

| Run # | Anti-foam | Anti-foam, ppm | | | |
|---|---|---|---|---|---|
| | | 2000 | 1000 | 500 | 250 |
| 1 | Unichem 7926 Coker Antifoam | none | none | very small initial amount | small amount |
| 2 | RNB30415 Coker Antifoam | none | very small initial amount | small amount | moderate amount |
| 3 | NEAT-10K Silicone Fluid | none | none | very small initial amount | small amount |
| 4 | NEAT-5K Silicone Fluid | none | none | very small initial amount | small amount |
| 5 | NEAT-1K Silicone Fluid | none | none | very small initial amount | small amount |
| 6 | UNICHEM 9850 Silicone emulsion | none | small amount | Moderate amount | |
| 7 | WATER 8000 ppm | does not affect foaming, sits on top of ammonia | | | |
| 8 | UI 7926 Coker Antifoam | none | none | very small initial amount | small amount |
| 9 | NEAT-1K Silicone Fluid | none | none | very small initial amount | small amount |

Chemical Make-up for antifoams
Unichem 7926
Kerosene <80%
Polydimethylsiloxane <30%
Naphthalene <5%
RNB-30415
Kerosene <90%
Polydimethylsiloxane <20%
Naphthalene <5%

The results show that the anti-foaming agents tested, neglecting water, were effective at eliminating foam. Generally, concentrations greater than 500 ppm seemed the most effective in the lab apparatus at atmospheric conditions.

More specifically, the results show that storage tank ammonia and cold ammonia foamed in similar manners and warm ammonia did not foam while being flashed/vaporized. All anti-foaming agents worked effectively to prevent the foaming of ammonia at various concentrations tested. The addition of lube oil to warm ammonia caused foaming. Foaming, caused by the addition of lube oil was also suppressed or prevented by adding anti-foam. Water had no effect on the foaming of ammonia—it appears that it neither enhances foaming, nor reduces foaming potentials.

EXAMPLE 2

This example illustrates the advantage of using the anti-foaming agent-containing ammonia in the production of a nitrile.

A typical arrangement for an ammonia vaporizing system consists of a vaporizer with a knock-out pot located in the overhead vapor line, a superheater located downstream of the knock-out pot, and a blowdown vessel with a heat source for minimizing ammonia in the blowdown exit. This particular vaporizer has a field instrument which measured pressure drop between the vapor space of the vaporizer and the knock-out pot. Foaming is detected by various sources: a significant rise in the vapor pressure drop to the knock-out pot, a rise in the level of the knock-out pot, a reduction in ammonia vapor temperature to the reactors because the superheater is contacting ammonia foam. Once the high pressure drop is detected, antifoam is added upstream of an ammonia control valve to enhance mixing and foaming is immediately suppressed as evidenced by a reduction in vapor pressure drop, reduction in knock-out pot level back to normal operating levels and an increase in ammonia supply temperature to the reactor.

During operation, reactor rates are lowered by as much as 10% due to the ammonia foaming because carryover of the foam affects the ammonia flowmeters, which impacts reactor computer, control and places the plant in an unstable situation. Also, foam in the vapor space in a vaporizer compromises the design of the relief valves on the vessel. Use of antifoam eliminates the 10% rate reduction and improves the safety of the process by eliminating the control swing and foam inlet the relief valves.

What is claimed is:

1. A composition comprising ammonia and an anti-foaming agent wherein said composition is substantially free of water and said anti-foaming agent is present in said composition in the range of from about 1 to about 5000 mg per kg of ammonia.

2. A composition according to claim 1 wherein said anti-foaming agent is present in said composition in the range of from about 5 to about 4000 mg per kg of ammonia.

3. A composition according to claim 1 wherein said anti-foaming agent is-present in said composition in the range of from 5 to about 3000 mg per kg of ammonia.

4. A composition according to claim 1 wherein said anti-foaming agent is selected from the group consisting of silicone, siloxane, polydimethyl siloxane, decane, and combinations of two or more thereof.

5. A composition according to claim 1 wherein said anti-foaming agent is polydimethyl siloxane.

6. A composition according to claim 3 wherein said anti-foaming agent is polydimethyl siloxane.

7. A process comprising contacting an ammonia-containing fluid with an anti-foaming agent to produce a foam-suppressed ammonia and vaporizing said foam-suppressed ammonia wherein said fluid is substantially free of water or is substantially anhydrous and said anti-foaming agent is present in said composition in the range of from about 1 to about 5000 mg per kg of ammonia.

8. A process comprising contacting an oxygen-containing fluid and a hydrocarbon with an ammonia vapor composition under a condition sufficient to effect the production of a nitrile wherein said composition comprises ammonia and an anti-foaming agent and is substantially free of water and said anti-foaming agent is present in said composition in the range of from about 1 to about 5000 ma per kg of ammonia.

9. A process according to claim 8 wherein said anti-foaming agent is present in said composition in the range of from about 1 to about 5000 mg per kg of ammonia, said hydrocarbon is an olefin, and said nitrile is hydrogen cyanide, acrylonitrile, methacrylonitrile, derivatives thereof, or combinations of two or more thereof.

10. A process according to claim 8 wherein said anti-foaming agent is present in said composition in the range of from 5 to about 2000 mg per kg of ammonia, said hydrocarbon is propane or propylene, and said nitrile is acrylonitrile.

11. A process according to claim 8 wherein said anti-foaming agent is selected from the group consisting of silicone, siloxane, polydimethyl siloxane, decane, and combinations of two or more thereof.

12. A process according to claim 9 wherein said anti-foaming agent is selected from the group consisting of silicone, siloxane, polydimethyl siloxane, decane, and combinations of two or more thereof.

13. A process according to claim 9 wherein said anti-foaming agent is polydimethyl siloxane.

14. A process according to claim 10 wherein said anti-foaming agent is polydimethyl siloxane.

15. A composition according to claim 2 wherein said anti-foaming agent is selected from the group consisting of silicone, siloxane, polydimethyl siloxane, decane, and combinations of two or more thereof.

16. A composition according to claim 2 wherein said anti-foaming agent is polydimethyl siloxane.

17. A composition according to claim 3 wherein said anti-foaming agent is polydimethyl siloxane.

18. A process according to claim 7 wherein said anti-foaming agent is selected from the group consisting of silicone, siloxane, polydimethyl siloxane, decane, and combinations of two or more thereof.

19. A process according to claim 7 wherein said anti-foaming agent is polydimethyl siloxane.

20. A composition according to claim 1 wherein said composition is a vapor.

* * * * *